United States Patent [19]
Hahn

[11] Patent Number: 5,912,233
[45] Date of Patent: *Jun. 15, 1999

[54] METHODS AND PEPTIDES FOR THE TREATMENT OF NON-IGE-MEDIATED DISEASES

[75] Inventor: Gary S. Hahn, Cardiff by the Sea, Calif.

[73] Assignee: Dura Pharmaceuticals, Inc., San Diego, Calif.

[ * ] Notice: This patent is subject to a terminal disclaimer.

[21] Appl. No.: 08/462,304

[22] Filed: Jun. 5, 1995

Related U.S. Application Data

[62] Continuation-in-part of application No. 07/942,671, Sep. 8, 1992, which is a continuation of application No. 07/878,867, May 5, 1992, which is a continuation-in-part of application No. 07/411,489, filed as application No. PCT/US87/03223, Dec. 9, 1987, which is a division of application No. 07/471,147, Jan. 26, 1990, Pat. No. 5,110,795, which is a continuation-in-part of application No. 07/382,623, filed as application No. PCT/US87/03222, Dec. 9, 1987, Pat. No. 5,061,692, and a continuation-in-part of application No. 07/411,489, said application No. 07/411,489, and application No. 07/382,623, which is a continuation-in-part of application No. 06/939,927, Dec. 9, 1986, Pat. No. 4,816,449, which is a continuation-in-part of application No. 06/899,891, Aug. 25, 1986, abandoned, which is a continuation of application No. 06/824,945, Feb. 3, 1986, Pat. No. 4,628,045, which is a continuation of application No. 06/746,175, Jun. 18, 1985, abandoned, which is a continuation-in-part of application No. 06/522,601, Aug. 12, 1983, abandoned.

[51] Int. Cl.⁶ .......................... A61K 38/00; A61K 38/02; C07K 5/00; C07K 7/00
[52] U.S. Cl. ............................................. 514/17; 530/330
[58] Field of Search .................. 514/16, 17, 18; 530/328, 329, 330, 331

[56] References Cited

U.S. PATENT DOCUMENTS 5,468,730  11/1995  Hahn ........................................ 514/17

*Primary Examiner*—Avis M. Davenport
*Attorney, Agent, or Firm*—Lyon & Lyon LLP

[57] ABSTRACT

Methods and compositions for the treatment of non-Ige-mediated inflammatory response or disease conditions are described.

16 Claims, 4 Drawing Sheets

METHODS AND PEPTIDES FOR THE TREATMENT OF NON-IGE-MEDIATED DISEASES

RELATED APPLICATIONS

The present application is a continuation-in-part of U.S. patent application Ser. No. 07/942,671, filed Sep. 8, 1992, which is a continuation of application Ser. No. 07/878,867, which was filed May 5, 1992. Ser. No. 07/878,867 is a continuation-in-part of Ser. No. 07/411,489, filed Nov. 23, 1989, which claims priority to International Patent Application No. PCT/US87/03223, filed Dec. 9, 1987; Ser. No. 07/878,867 is also a divisional of Ser. No. 07/471,147 (now U.S. Pat. No. 5,110,795), filed Jan. 26, 1990, which is a continuation-in-part of Ser. No. 07/382,623 (now U.S. Pat. No. 5,061,692), filed Nov. 23, 1989, which claims priority to International Patent Application No. PCT/US87/03222, filed Dec. 9, 1987. Ser. No. 07/471,147 is also a continuation-in-part of Ser. No. 07/411,189. Each of these PCT applications is a continuation-in-part of U.S. application Ser. No. 939,927, filed Dec. 9, 1986 and now U.S. Pat. No. 4,816,449. U.S. Pat. No. 4,816,449 is a continuation-in-part of Ser. No. 899,891 (filed Aug. 25, 1986 and now abandoned) which is a continuation of Ser. No. 824,945 (filed Feb. 3, 1986, and now U.S. Pat. No. 4,628,045), which is a continuation of Ser. No. 746,175 (filed Jun. 18, 1985 and now abandoned), which is a continuation-in-part of Ser. No. 522,601 (filed Aug. 12, 1983 and now abandoned). The entire disclosures of the foregoing applications and patents are incorporated herein by reference.

BACKGROUND

The immune system of humans and animals normally functions to protect its host from infectious organisms or from cancerous transformation by host cells. In many instances however, the immune system manifests a response that itself results in considerable damage to otherwise healthy cells and organs. Such over-reactivity of immune responsiveness is responsible for many serious conditions or diseases including allergies and autoimmune diseases.

In order to classify the processes by which the immune system produces cellular damage, immunologists have divided immune responses into four broad classes (Type I, II, III and IV) (Roitt, I. M., et al., *Immunology*, C. V. Mosby, N.Y., 1985, p. 19.1).

Type I responses are also called immediate hypersensitivity reactions and include those diseases which produce the symptoms classically associated with "allergies" or the "allergic syndrome" including allergic rhinitis (hay fever), allergic asthma, allergic conjunctivitis and allergic reactions to insect stings or foods. These conditions are characterized by a rapid clinical manifestation of allergic symptoms within minutes after exposure to an antigen (allergen) to which the subject has been previously sensitized.

In order for Type I hypersensitivity to occur, a specialized sequence of events within mast cells and basophils must be triggered by immunoglobulin E (IgE) antibodies that have been manufactured within the body. In this process, IgE directed toward an antigen (allergen) must bind to receptors on mast cells and basophils which specifically bind to the Fc region of IgE. Mast cells and basophils that have allergen-specific IgE bound to them are considered to be sensitized or "armed" for subsequent exposure to allergen. Should allergen be introduced into the local environment of the mast cells or basophils, the cells are automatically stimulated or "triggered" to release histamine and other vasoactive chemicals which produce the familiar "allergic symptoms" characteristic of allergic disease.

The hypersensitivity states characterized by types II, III and IV hypersensitivity are distinguished from type I hypersensitivity by many distinct and diverse features.

Type II hypersensitivity occurs when IgG or IgM antibodies bind to antigens located on the surfaces of cells. Such binding is mediated by the antibodies' Fab arms which contain specific structures that recognize cell surface antigens. Upon binding, the Fc regions of IgG or IgM interact with the complement system (a family of inflammatory and cell-killing molecules) or immune system "killer" cells bearing IgG or IgM Fc receptors. Some examples of diseases in which type II hypersensitivity reactions predominate include transfusion reactions, hemolytic disease of the newborn, autoimmune hemolytic anemias, hyperacute graft rejection, Goodpasture's syndrome, myasthenia gravis and other conditions.

Type III hypersensitivity is produced when complexes or aggregates of antibodies (usually IgG or IgM) and soluble antigens form in abnormally large amounts and activate the complement inflammatory system. Some examples of diseases in which type III hypersensitivity reactions are pathogenically important include systemic lupus erythematosus, rheumatoid arthritis, polyarteritis and other forms of vasculitis, fibrosing alveolitis and many infectious diseases, especially bacterial endocarditis, hepatitis and malaria.

Type IV hypersensitivity (delayed-type hypersensitivity), by contrast to the other three hypersensitivity reactions, is triggered primarily by T cells having specialized T cell receptors able to recognize and bind to the specific sensitizing antigen on a cell's surface. Upon reexposure to an antigen, T cell receptor molecules bind to the antigen and trigger a complex series of events that result in secretion of lymphokines and other regulatory molecules that recruit new cells leading ultimately to the destruction of the antigen-bearing cell. Delayed type hypersensitivity, as its name implies, has a delayed onset of inflammation that ranges from about 24 hours to several days after reexposure to the sensitizing antigen. Diseases in which type IV hypersensitivity is believed to play an important pathogenic role are frequently termed "T-cell mediated" to reflect the unique role played by the T-cell in recognizing the sensitizing antigen. These diseases include multiple sclerosis, rheumatoid arthritis, juvenile onset diabetes mellitus, ulcerative colitis, and regional enteritis (Crohn's disease), among others.

An important principle that distinguishes type I hypersensitivity (allergy) from the other hypersensitivity states discussed above is that the allergic inflammation begins within minutes after allergen exposure. By contrast, other hypersensitivity states exhibit inflammation only after hours to days following reexposure to the sensitizing agent.

A second important principle that distinguishes type I hypersensitivity from other hypersensitivity states is the source of the sensitizing agent. In type I hypersensitivity, the sensitizing agent (allergen) is not a part or component of the host body. Instead, the allergen is a substance found outside of the host body that is later introduced into the body by exposure to the environment. Types II, III and IV hypersensitivity, by contrast, may have immune responses directed towards antigens located on cells and molecules that are normal constituents of the body. Such immune responses toward normal constituents of the body are termed "autoimmune diseases" and constitute a medically important class of diseases distinct from allergic diseases.

A third important principle that distinguishes type I hypersensitivity from other hypersensitivity states is the degree to which cell killing occurs. In type I hypersensitivity, the IgE-mediated triggering reaction which causes the release of vasoactive allergic mediators does not result in the death of the releasing mast cell or basophil. Instead, the "trigger" reaction is the result of an active secretory process that may recur after a length of time. Similarly, the effect of the vasoactive allergic mediators on surrounding cells is regulatory, not cytotoxic. Allergic mediators serve to increase the permeability of small blood vessels and activate a variety of vasoregulatory and immunoregulatory processes that do not normally result in cell death. Types II, III and IV hypersensitivity, by contrast, have as a principal function cell killing reactions which normally lead to the destruction of infectious agents or cancer cells.

In 1975, Hamburger reported that a pentapeptide with a sequence derived from the constant domain of human IgE could inhibit a local cutaneous allergic reaction (Prausnitz-Kustner) by approximately 90% (Hamburger, R., Science 189:389 (1975); U.S. Pat. Nos. 4,171,299 and 4,161,522). This pentapeptide, Asp-Ser-Asp-Pro-Arg, is known as pentigetide. The peptide has been shown to inhibit systemic allergic disease in humans after injection by the subcutaneous route.

U.S. Pat. No. 4,628,045 describes a peptide having the amino acid sequence Asp-Ser-Glu-Pro-Arg. The peptide is an "active site" peptide which is capable of blocking immune complex binding to immunoglobulin Fc receptors. The patent also discloses particular activity of the peptide Asp-Ser-Asn-Pro-Arg in inhibiting rosette formation involving IgE Fc receptors on basophils and monocyte/macrophages. U.S. Pat. No. 4,161,522, issued Jul. 17, 1979 to Hamburger, reports that the peptide Asp-Ser-Asn-Pro-Arg exhibited activities of 5% and 6% in two trials which measured the ability of the peptide to block binding of IgE to lymphoblastoid tissue culture cells. Other peptides, including Asn-Ser-Asp-Pro-Arg and Asn-Ser-Asn-Pro-Arg were reported to exhibit lower activity, whereas the dimer [-Cys-Ala-Asn-Ser-Asn-Pro-Arg]$_2$ exhibited activity of 9% and 12%. Such peptides, including pentigetide, are stated to be useful in blocking the human allergic response.

All publications, patents and other reference materials referred to in the present specification are incorporated herein by reference.

SUMMARY OF THE INVENTION

The present invention also discloses the surprising finding that pentigetide and a number of pentapeptides disclosed in U.S. Pat. No. 4,816,449 not only have antiallergic (anti-type I hypersensitivity) activity as specified by U.S. Pat. Nos. 4,161,522 and 4,171,299, but also have additional, unexpected medically useful properties as well. By contrast, the two cited patents disclose only that pentigetide has antiallergic (anti-type I hypersensitivity) activity. As will be presented in the present application, allergies or the "allergic syndrome" are medical conditions clearly distinct from the new disease applications disclosed in the present invention.

Specifically, pentigetide and the peptides disclosed herein have a general anti-inflammatory activity in addition to their antiallergic anti-inflammatory activity. The anti-inflammatory activity described in the present invention is broad and extends to diseases and conditions other than IgE-mediated disease conditions. In particular, pentigetide has been shown to have anti-inflammatory activity with respect to inflammatory bowel diseases and conditions including ulcerative colitis and regional enteritis (Crohn's disease).

Therapeutic antiallergic agents only rarely exhibit therapeutic activity in the non-allergic diseases and conditions disclosed in the present invention. For example, the commonly used therapies for allergic disease include antihistamines, cromolyn sodium, immunotherapy, alpha adrenergic agonists (vasoconstrictors), beta adrenergic agonists (bronchodilators), methylxanthine preparations (e.g., theophylline), mucolytics, expectorants and steroids. Of these therapeutics, only steroids exhibit anti-inflammatory activity in allergic diseases and non-allergic diseases such as inflammatory bowel disease.

More specifically, pentigetide and the present peptides are able to suppress inflammation caused by a range of inflammatory reactions common to type II, III and IV hypersensitivity reactions which have been implicated in the pathogenesis of inflammatory bowel diseases, and inflammatory reactions produced by the application or exposure of the body or its parts to irritating or inflammation-producing agents.

This surprising discovery strongly suggests that pentigetide and these peptides are useful in the treatment of a variety of non-allergic (non-type I hypersensitivity) conditions or diseases previously discussed. It additionally suggests that pentigetide and its biologically active analogs are useful in treating and/or preventing inflammatory conditions not produced by an immune response to antigens, but instead by exposure of the body to noxious, irritating or otherwise harmful substances or stimuli produced by chemicals (such as formalin and IgG immune complexes and other irritating chemicals such as Vitamin A and its derivatives (retinoids, including tretinoin and related compounds)), electromagnetic irradiation (e.g., sunburn) or other agents or processes, which produce irritation or inflammation. Additional examples of chemical components which are potential sources of irritation or inflammation are described in applicant's co-pending application Ser. No. 08/362,100, the disclosure of which is incorporated herein by reference.

Often, potentially irritating chemical ingredients are found in cosmetic substances. Examples of cosmetic substances, including such cosmetic substances that are potential sources of irritation or inflammation, are described in applicant's co-pending application Ser. No. 08/362,100, the disclosure of which is incorporated herein by reference.

It has also been discovered that the compound Asp-Ser-Asn-Pro-Arg, like pentigetide, has general anti-inflammatory activity as disclosed herein, and in particular is active in reducing or preventing inflammation associated with inflammatory bowel diseases such as ulcerative colitis and regional enteritis or Crohn's disease.

DETAILED DESCRIPTION

Figure 1A:
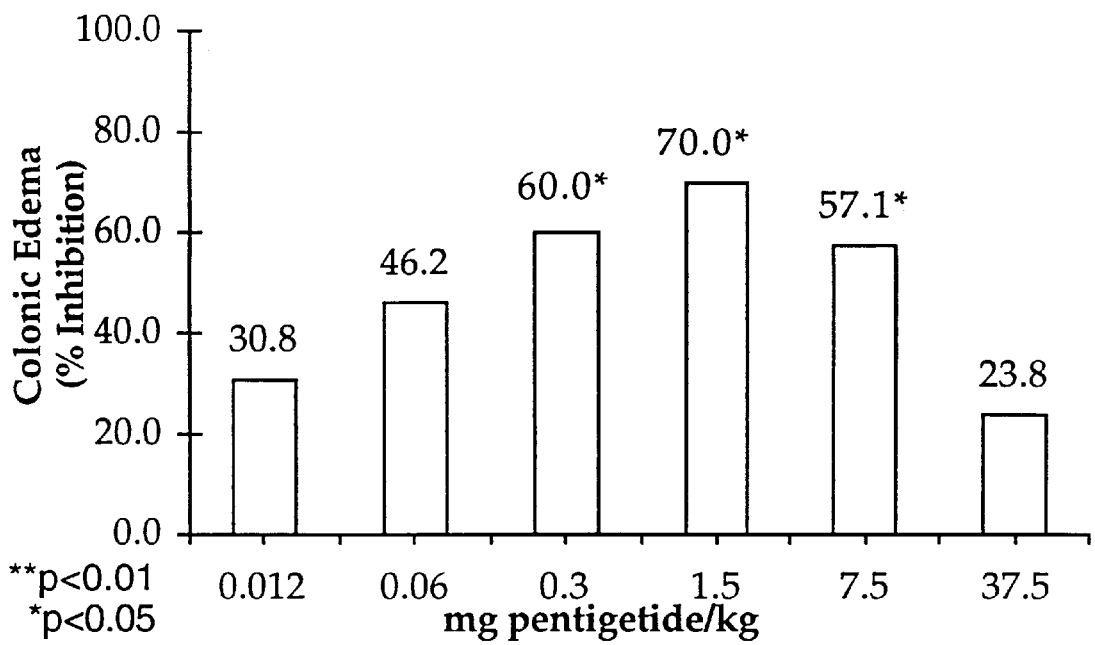
FIGS. 1a and 1b depict the inhibition of colonic edema and colitic signs in mice as a function of dosage of the peptide Asp-Ser-Asp-Pro-Arg.

The present invention relates to peptides useful in treating disease conditions not mediated by IgE, as well as to methods for treating such diseases using the described peptides, including using pentigetide or the compound Asp-Ser-Asn-Pro-Arg. In particular, the invention relates to peptides having a pentapeptide structure denoted herein as A-B-C-D-E, wherein the letters represent amino acid residues linked in the conventional amino-to-carboxyl direction. Individually, the amino acids are selected from the groups comprising, for A, Asp or Glu;

for B, Ser, D-Ser, Thr, Ala, Gly or Sarcosine;

for C, Asp, Glu, Asn or Gln;

for D, Pro, Val, Ala, Leu or Ile; and for E, Arg, Lys or Orn.

As used herein, the above three-letter abbreviations are those conventionally used for amino acids and represent both D- and L-forms of such amino acids. L-forms are particularly preferred, although D-Ser is also a preferred amino acid in the B-position of the above peptides. Particularly preferred sequences are specified in the appended claims. Asp-Thr-Glu-Ala-Arg is a preferred peptide.

In addition to peptides and their pharmaceutically acceptable salts formed by simple substitution of amino acids in the respective positions as indicated above, substituted or otherwise derivatized peptides and salts thereof are also within the scope of the present invention. Preferred substituents include N-alpha acyl substituents at the amino terminus of the peptides of the form RCO—, where R is alkyl, alkenyl or alkynyl (either unbranched or branched, and preferably from 1 to about 8 carbons), or aryl, alkaryl, aralkyl or cycloalkyl (preferably of from about 6 to about 18 carbons); C-terminal substituents of the form —NHR$^1$ or —NR$_2^1$ (where each R$^1$ is independently hydrogen, alkyl, alkenyl or alkynyl (preferably of from 1 to about 8 carbons), or aryl, alkaryl, aralkyl or cycloalkyl (preferably of from about 6 to about 18 carbons); C-terminal substituents of the form —OR (where R is as defined above); and des-alpha-amino derivatives of such peptides wherein the alpha-amino group of one or more amino acid residues is absent. An amino-terminal acetyl substituent is a particularly preferred substituent. Pharmaceutically acceptable acid or base addition salts of such peptides are also contemplated herein.

Preferred substituents include substituents at the amino terminus of pentigetide of the form RCO—, or R—, C-terminal substituents of the form —NH$_2$, —NHNH$_2$, —NHR or —NR$_2$ and C-terminal substituents of the form —OR, where each R is independently a linear or branched unsubstituted or substituted alkyl, alkenyl or alkynyl (either unbranched or branched, and preferably from 1 to about 8 carbons), or aryl, alkaryl, aralkyl or cycloalkyl (preferably of from about 3 to about 18 carbons), or, in the case of —NR$_2$, the R—groups are together a cyclized group forming (in attachment with the nitrogen atom) a 5-8 med saturated heterocyclic ring optionally containing an oxygen or nitrogen as a further ring heteroatom.

An amino-terminal acetyl substituent is a particularly preferred substituent, and propionyl, benzoyl and adamantyl—CH$_2$CO—substituents are also preferred. Amidating or esterifying carboxyl-terminal substituents formed from unsubstituted or lower alkyl-substituted amino, or from lower alkoxy or single-ring aryloxy, groups are preferred, and groups of the form —NH$_2$, —NHCH$_3$, —OCH$_3$ and —O(C$_6$H$_5$) are especially preferred. Amidating substituents are particularly preferred. Where an amidating group of the structure —NR$_2$ is to be cyclic in form, the N-morpholino heterocyclic structure is preferred. The use of such substituents on the amino and/or carboxyl terminus of the compound will tend to protect the peptide from metabolism in the in vivo environment and thereby increase the effective half-life of the compound in the body. Pharmaceutically acceptable acid or base addition salts of pentigetide and its derivatives are also contemplated herein.

Where one or more R groups is itself additionally substituted, preferred substituents include hydroxyl, amino, lower (C$_1$–C$_8$) alkoxyl, and, in the case of aromatic R groups, the foregoing substituents as well as nitro, chloro and bromo moieties. Such substituents may be used, for example, to alter bioactivity, solubility and/or biodistribution characteristics of the subject peptides. Where R includes an aryl group, substituents occurring on the meta and/or para positions (i.e., 3'-and/or 4'-positions) are most preferred. Preferred alkaryl forms of R include (3'-methyl)phenyl and (4'methyl)phenyl groups.

Similarly, substituted or otherwise derivatized forms, such as those described immediately above, of the compound Asp-Ser-Asn-Pro-Arg are also within the scope of the present invention. Pharmaceutically acceptable salts of Asp-Ser-Asn-Pro-Arg and its derivatives are also contemplated.

In addition to the above pentapeptide embodiment, the present invention also relates to the following peptides and their uses as described herein:

Ala-Asp-Ser-Asp-Pro-Arg,

Ser-Asp-Pro-Arg,

Asp-Pro-Arg, as well as acyl, amide and ester derivatives of these peptides as described above, and pharmaceutically acceptable salts of such peptides.

The peptides and derivatives as described above may be used in the treatment of various inflammatory disease conditions initiated by biological systems or pathways other than IgE. Particular examples of such non-IgE-mediated disease conditions are noted above in the discussion of Type II, III and IV hypersensitivity responses, and include a broad range of inflammatory conditions that are substantially non-allergic (non-type I hypersensitivity), i.e., non-IgE-mediated, in nature. Additional examples of such disease conditions are discussed in U.S. Pat. No. 4,628,045, the disclosure of which is incorporated herein by reference, and are contemplated to be within the scope of the present invention. By way of further example, the breadth of the present invention is illustrated by the fact that certain of the present peptides are useful in inhibiting inflammation mediated by the arachidonic acid pathway, which is invoked in a wide variety of allergic and non-allergic disease conditions. Thus, inflammatory diseases which involve in substantial part non-IgE-mediated mechanisms, even if in contribution with IgE-mediated mechanisms, may be expected to be inhibited or prevented to an enhanced degree by virtue of the activity of the peptides against one or more disease-contributive non-IgE-mediated disease mechanisms.

The following examples and the disclosure of U.S. Pat. No. 4,816,449 relate to the utility of the present peptides in treating such non-IgE-mediated inflammatory disease conditions.

EXAMPLE 1

Pentigetide Inhibition of Type IV Hypersensitivity

Type IV hypersensitivity (delayed-type hypersensitivity or DTH), as previously described, is triggered primarily by T cells having specialized T cell receptors able to recognize and bind to the specific sensitizing antigen on a cell's surface. Upon reexposure to an antigen, T cell receptor molecules bind to the antigen and trigger a complex series of events that result in secretion of lymphokines and other regulatory molecules that recruit new cells leading ultimately to the destruction of the antigen-bearing cell.

DTH may be readily induced in animals by the appropriate exposure of animals to sensitizing antigens known to elicit a DTH response. Lagrange, P. H., et al., J. Exp. Med. 139:528 (1974). In order to assess the effect of pentigetide in suppressing the inflammation of DTH, two antigens were used. The first antigen, tetanus toxoid, is a chemically modified derivative of the tetanus toxin molecule. Tetanus toxoid was selected because it represents a single molecule that has few regions that act as antigens in a DTH response. The second antigen used to induce DTH was sheep erythrocytes, including the entire red blood cell which contains many different molecules which may simultaneously be recognized as antigens for T cells during the DTH response.

Tetanus toxoid-induced DTH reactions were elicited in approximately 60-day-old female Balb/C mice by injecting 25 mcg of tetanus toxoid (Mass. Dept. of Public Health, Lot No. LP 457 PR) subcutaneously in a 0.7 ml volume of saline containing 35.7 mcg tetanus toxoid/ml distributed between three dorsal injection sites at the beginning of each experiment (day "0").

Either saline or various amounts of pentigetide were then injected in 0.2 ml volumes at the nape of the neck on day 3, 4 and 5 after tetanus toxoid immunization. A "positive control" substance, indomethacin, was also administered on day 4.

On day 5, the right hind footpad of mice was challenged with 0.057 mg tetanus toxoid in a volume of 0.025 ml. The left hind footpad was uninjected and served as a control. Approximately 24 hours later, the mean footpad volumes for injected ("challenged") and uninjected ("control") footpads were measured using a Buxco plethysmograph and compared. Evaluation of inflammation inhibition for pentigetide or indomethacin was performed by calculating the percent change of the mean difference in volume of the challenged footpad versus the control footpad from drug or saline-injected mice. In these experiments, 97 mice served as saline-injected controls. The number of mice at each dose group is designated by n.

TABLE 1

| Pentigetide Dose (mg/kg) | Percent Inhibition |
| --- | --- |
| 1.0 (n = 25) | 7 |
| 2.0 (n = 25) | 14 |
| 4.0 (n = 31) | 20 |
| 20.0 (n = 31) | 19 |
| 50.0 (n = 10) | 40 |

Indomethacin (1.0 mg/kg, n=41) provided 45% inhibition.

In the second test, sheep erythrocyte (SRBC)-induced DTH reactions were elicited in approximately 60-day-old female Balb/C mice by injecting 0.2 ml of a 0.01% suspension of SRBC intravenously in the tail vein at the beginning of each experiment (day "0"). Either saline or various amounts of pentigetide were then injected in 0.2 ml volumes at the nape of the neck on day 2, 3 and 4 after SRBC immunization. A "positive control" substance, indomethacin, was also administered on day 4.

On day 4, the right hind footpad of mice were challenged with 0.025 ml of a 20% SRBC suspension. The left hind footpad was uninjected and served as a control. Approximately 24 hours later, the mean footpad volumes for injected ("challenged") and uninjected ("control") footpads were measured using a Buxco plethysmograph and compared. Evaluation of inflammation inhibition for pentigetide or indomethacin was performed by calculating the percent change of the mean difference in volume of the challenged footpad versus the control footpad from drug or saline-injected mice. The number of mice at each dose group is designated by n.

TABLE 2

| Pentigetide Dose (mg/kg) | Percent Inhibition |
| --- | --- |
| 1.0 (n = 21) | 8 |
| 10.0 (n = 22) | 19 |
| 100.0 (n = 55) | 23 |
| 400.0 (n = 30) | 36 |
| 800.0 (n = 29) | 41 |

Indomethacin (1.0 mg/kg, n=27) provided 43% inhibition.

The higher dose of pentigetide needed to provide substantial DTH inhibition is a reflection of the difference in the nature of the antigens used to elicit the DTH response. This dose difference illustrates that the dose of pentigetide needed to inhibit DTH in human disease may vary greatly depending on the nature of the antigens involved in the DTH response. For example, sheep erythrocytes are intact cells and as such present the immune system with many varied structures that may act as sensitizing antigens including many proteins, complex carbohydrates, lipids and molecules that are conjugates of proteins, carbohydrates and lipids. Tetanus toxoid, by contrast, is a single protein molecule and therefore contains only a few structures able to act as antigens under the experimental conditions employed in these examples. It is to be expected, therefore, that the amount of pentigetide needed to suppress the inflammation produced by these two antigens would differ, as the data presented suggests.

It is similarly expected that the dose of pentigetide needed to provide a therapeutic effect in the treatment of non-allergic diseases of conditions (e.g., autoimmune diseases or other types of hypersensitivity conditions) may substantially vary depending on the disease or condition, stage of disease, route of pentigetide administration and other factors. Indeed, the dose response curve associated with the non-IgE-mediated inflammatory inhibition of the present peptides may in some cases be complex, although routine experimentation with various doses and systems can be expected to yield therapeutically effective doses.

EXAMPLE 2

Pentigetide Inhibition of Carrageenan-Induced Edema

Carrageenan is a sulphated polygalactan compound derived from certain algae that is widely used as an inflammatory-inducing agent in experimental animal models of inflammation (Thomson, A. W., et al. Agents and Actions, 11:265, 1981). By contrast to tetanus toxoid, SRBC and other inflammation-producing agents, carrageenan does not produce inflammation by the elicitation of an antigen-specific immune response towards itself.

Instead, the inflammatory reaction induced by carrageenan is produced by the non-specific activation of many inflammatory pathways including: complement, clotting, kinin, prostaglandin, leukotriene and superoxide production systems. Activation of these inflammatory pathways is simultaneously accompanied by the release of preformed inflammatory mediators such as histamine and serotonin. Additionally, carrageenan is selectively toxic to macrophages causing them to release cytotoxic and inflammatory proteases and other substances from disrupted lysosomes (Baker, K. C., et al., Fd. Chem. Toxic 24:891, 1986; Crunkhorn, P., et al. Br. J. Pharmac. 42:392, 1971).

The ability of carrageenan to activate the complement inflammatory system and many other inflammatory pathways resembles the broad activation that occurs in types II and III hypersensitivity in which complement activation plays a principal role in inducing inflammation. Activated complement, for example, like carrageenan, can rapidly cause cell lysis and cytotoxicity while simultaneously activating a broad range of additional inflammatory pathways.

In order to examine the ability of pentigetide to inhibit carrageenan-induced inflammation, female Balb/C mice were injected with 0.025 ml of 1.0% carrageenan solution (type lx carrageenan: Sigma No. C-1013, Lot No. 86F-0698) or saline in the right hind footpad 5 minutes after intravenous tail vein injection of 0.2 ml pentigetide (1.0 mg/kg) or saline solution. Indomethacin (10 mg/kg was used as a positive control and was administered by subcutaneous injection 24 hours prior to carrageenan injection. Footpad volumes were measured using a Buxco plethysmograph over a 6 hour period. Pentigetide produced substantial inhibition of carrageenan-induced inflammation when compared to saline control animals.

TABLE 3

| Hours After Carrageenan Injection | Percent Inhibition | |
|---|---|---|
|  | Pentigetide (1.0 mg/kg) | Indomethacin (10 mg/kg) |
| 1.0 | −2 | −35 |
| 2.0 | −51 | −60 |
| 4.0 | −19 | −39 |
| 6.0 | −34 | −47 |

These surprising findings indicate that pentigetide can suppress the inflammation produced by activation of the complement system and the other inflammatory pathways activated by carrageenan. Since complement activation is a principal component of inflammation produced during type II and type III hypersensitivity reactions, Pentigetide can have an important therapeutic effect in diseases having hypersensitivity types II and III as components of their pathogenesis.

EXAMPLE 3

Pentigetide Inhibition of Non-Allergic Urticaria

Conventional "allergic" urticaria is an IgE-mediated condition that is usually self-limiting. It represents a temporary allergic response to drugs, foods, infection or exposure to environmental conditions such as cold, heat, pressure or light. Allergic urticaria requires the combination of an antigen and IgE to mediate the release of histamine from basophils and mast cells. The histamine triggers vasodilation and increased vascular permeability as well as an axon reflex that increases swelling. Chronic refractory idiopathic urticaria (CRIU) is a non-allergic condition commonly known as "hives". Its symptoms include pruritus (itching) and the appearance of erythematous skin elevations and lesions. In contrast to allergic urticaria, it is not traceable to a particular etiologic agent and is not self-limiting (the designation "chronic" generally being given when the urticaria persists for more than six weeks). CRIU is not IgE mediated, and patients who suffer from the condition frequently display normal levels of IgE. Existing therapy for CRIU is merely supportive. Antihistamines such as hydroxyzine (Atarax), cyproheptadine (Periactin) and diphenhydramine (Benadryl) are used for the relief of pruritus but such agents have little effect on the appearance of the lesions. Other treatments include the use of steroids in severe cases; however, the risks associated with long-term steroid administration restrict any such therapy. Moreover, some patients are unresponsive to both antihistamines and steroid, leaving no specific therapy available to them until the present invention. Kaplan, A. P., in *Allergy: Principles and Practice*, eds. Middleton, E., et al., 2d ed. (Mosey Co., St. Louis: 1983), p. 1341.

Clearly, existing methods of treating the non-IgE mediated condition of CRIU are not satisfactory. It is one surprising discovery of this invention that when the present peptides are administered in therapeutic doses, they may provide an effective treatment for CRIU. Thus, the therapeutic administration of Pentigetide to patients suffering from CRIU may significantly relieve the discomfort associated with those conditions in the absence of any known side-effects.

Two female patients (A and B) with chronic idiopathic urticaria were selected for treatment with pentigetide on a compassionate need basis. The selection was based on the presence of non-allergic (non-IgE-mediated) urticaria uncontrolled by tolerated doses of antihistamines and the absence of any other known diseases. The patients, whose urticaria was so severe as to interfere with their normal activities and work, wished to avoid the addition of corticosteroids to their treatment regime. Prior to the treatment, the patients signed approved consent forms and FDA approval was obtained. The doses were prepared from 50 mg of lyophilized pentigetide reconstituted into one ml water immediately before each subcutaneous injection.

Patient A, a 57-year-old Caucasian female with chronic idiopathic urticaria of unknown etiology, did not respond to maximum doses of H1 and H2 antagonists. Prior to pentigetide treatment, as described here, she had 30 to 40 severely itchy hives per day. The disfigurement and discomfort associated with her urticaria significantly interfered with her daily activities. She received 50 mg of pentigetide subcutaneously in each arm (total dose: 100 mg) on a Monday, Wednesday and Friday basis for a total of six treatments over two weeks. Preceding the pentigetide treatment, she had been maintained on a combination of 50 mg Atarax 4 times a day and 300 mg cimetadine 4 times a day; this treatment continued during the pentigetide treatment. Forty-eight hours after initial Pentigetide therapy, A's hives decreased to 5–10 per day and remained at that level throughout the two week period. Patient A also suffered from severe seasonal allergic rhinitis which totally resolved within 24 hours of initial pentigetide therapy and remained in remission throughout the treatment. There was no experience of adverse side effects throughout the two week treatment, however, the urticaria re-evolved after pentigetide was discontinued.

Patient B, a 62-year-old Caucasian female, suffered for 17 years from chronic idiopathic urticaria unresponsive to conventional antihistamine therapy. She was seen at both the National Institute of Heath and the Mayo Clinic without therapeutic success. Her condition was controlled only through the use of moderate to high doses of corticosteroids which still left the hives nodular and highly pruritic. Antihistamines provided no therapeutic value. Prior to pentigetide treatment, she was maintained on 1.5 mg Decadron every other day. With that treatment, her hive count was greater than 100 a day.

Patient B's pentigetide treatment was identical to that of Patient A. Within 24 hours of treatment with pentigetide, she experienced marked improvement. After two days of therapy, her hive count was reduced to less than 10 per day with an almost total resolution of pruritus. On the sixth day of pentigetide injections, there was no more evidence of nodular urticarial lesions although a patch of fine, maculopapular rash remained on her right flank. She did not experience any side effects from the treatment and reported that she had never shown such a dramatic improvement in her condition except with high doses of corticosteroids. Following this improvement, Patient B's treatment was continued at 100 mg subcutaneously twice, rather than three times, a week for another two weeks, followed by a reduction to 50 mg twice per week. Total relief for the urticaria continued at this level.

The following example further demonstrates the utility of pentigetide and Asp-Scr-Asn-Pro-Arg in treating non-IgE-mediated inflammatory disease conditions.

EXAMPLE 4

Pentigetide Inhibition of Type III Hypersensitivity a. Inflammatory Bowel Disease Model A mouse model of intestinal inflammation was employed wherein the efficacy of pentigetide in reducing inflammation induced by formalin and complementfixing IgG immune complexes was measured. This model is particularly useful as a model of human ulcerative colitis and shares many clinical and histological functions of the human disease including sensitivity to glucocorticoids, sulfasalazine and 5-aminosalicylic acid (see L. P. Walsh, et al., British J. Pharm. 91:294 (1987); A. Blackham, et al., British J. Pharm. 89:694 (1986); L. D. Walsh and I. J. Zeitlin, British J. Pharm. 92:741 (1987)). The mouse model of intestinal inflammation used in these studies is induced by the exposure of the animals to chemicals which are known to trigger inflammatory processes in both animals and humans. The first step in inducing inflammation in this model is the exposure of tissues to formalin (an aqueous solution of formaldehyde gas), which is known to produce irritation and inflammation upon contact with cells of animals or humans (Clinical Toxicology of Commercial Products (R. E. Gosselin, et al., editor), 5th edition, Williams & Wilkins, 1984, pp. III-196 to III-198). At the peak of formalin-induced inflammation, IgG immune complexes are injected to further activate inflammatory processes which involve activation of leukocytes and the complement system. Inflammation induced by immune complexes is classified as Type III hypersensitivity and contributes to many disease processes, some of which were previously discussed.

In the present measurements, three trials were used: a dose-response trial, a "therapeutic"-vs.-"prophylactic" treatment trial, and a trial which compared pentigetide to Asp-Ser-Asn-Pro-Arg, control peptides and to a vehicle control solution.

In the immune complex-mediated ulcerative colitis model employed, intestinal inflammation was induced in male BKA mice (outbred Swiss albino) (20–30 g) using the method described by Walsh in mice (i.e., Walsh, et al., British J. Pharm. 91:294, 1987) and by Hodgson in rabbits (Hodgson, et al., Gut 19:225 (1978)). As a primary irritant, 1% formalin in saline was instilled intra-rectally into mice. Three hours later, at the peak of the initial formalin response, immune complexes composed of polyclonal rabbit anti-human serum albumin (HSA) (Sigma) formed in antigen excess were injected i.v. The resultant colitic inflammation reached a maximum three days later. Mice were then sacrificed for evaluation.

Peptides were synthesized by the solid phase method and purified by high performance liquid chromatography. Prior to packaging, all peptides were filter sterilized using 0.22u filters. Packaged peptides were randomly selected and found free of endotoxin using the limulus amebocyte lysate assay (Whittaker Bioproducts).

Colonic tissue water content was determined by tissue weight loss on drying of colonic tissues. Colitic sign scores were evaluated using a single point assignment for the presence of each of the parameters listed in Table 4.

TABLE 4

Parameters Used for the Assessment of Colitis (Colitis Score)
One point assigned for the presence of each of the following parameters:

| Clinical symptoms of colitis: | Diarrhea |
| --- | --- |
| | Rectal hemorrhage |
| Macroscopic features of the colon: | Edema |
| | Erythema |
| | Ulceration |
| | Stricture formation |
| | Mucous |

Each experiment consisted of (A) a group of untreated healthy mice (n=10), (B) a vehicle treated control group which had received only intra-rectal formalin solution (n=10), (C) a group of formalin+IgG-anti HSA-treated mice given s.c. saline injections and (D) one or two formalin and IgG-anti HSA experimental drug treatment groups (n=10).

The response to immune complex alone was determined quantitatively by subtracting the mean value in group B from the mean value in group C. An estimate of the percentage reduction in this response produced by the drug was calculated as:

$$\text{Percentage Reduction} = 100 \cdot \frac{(\text{Group C}) - (\text{Group D})}{(\text{Group C}) - (\text{Group B})}$$

Group A animals (healthy) were used as a baseline to monitor Group B animals (formalin instillation only). Since the formalin-induced inflammation is transient, any inflammation present in the formalin only group (compared with healthy group A) at sacrifice on day 3 would constitute evidence that an unknown source of inflammation was present and all results from that particular experiment would be discarded. Statistical significance was determined using the non-parametric Mann-Whitney U-test.

b. Peptide Administration

Dose-Response Trial

In order to establish a dose-response profile for pentigetide, animals received 0.012, 0.06, 0.3, 1.5, 7.5 or 37.5 mg pentigetide/kg subcutaneously 1 day prior and 1 hour prior to induction of colitis and daily for a further 3 days until sacrificed. Vehicle control or control peptides were administered to control groups in the same volume and according to the same schedule as pentigetide. Prednisolone (5 mg/kg) was administered i.p. daily for three days prior to induction of colitis and subsequently daily for a further 3 days as a positive control.

Therapeutic-vs.-Prophylactic Trial

A "therapeutic" administration schedule was used to test whether pentigetide could suppress an ongoing inflammatory response by first injecting pentigetide after the administration of formalin and immune complexes. Therapeutically treated mice were given 1.5 mg pentigetide/kg s.c. 3 hours post-immune complex (6 hours post-formalin) and daily thereafter.

A second "prophylactic" treatment regimen was used to determine whether pentigetide could suppress inflammation if injected immediately prior to immune complex administration. In this study, 1.5 mg/kg pentigetide was first injected s.c. 1 hour prior to intra-rectal formalin and daily thereafter. Prednisolone (5.0 mg/kg) was used as a positive control and injected i.p. 3 days, 2 days, and 1 day prior to, and on the day of, formalin and immune complex administration and then daily thereafter for three days.

Control Peptide and Asp-Ser-Asn-Pro-Arg Trial

In these experiments, mice were treated with one of the following peptide or vehicle control solutions A, B, C, D or E:

A Pentigetide (Asp-Ser-Asp-Pro-Arg [DSDPR])
  B Asp-Ser-Asn-Pro-Srg (DSNPR)
  C Phosphate buffered saline
  D A scrambled pentigetide sequence (Asp-Pro-Asp-Arg-Ser [DPDRS])
  E A second control peptide (Pro-Ser-Lys-Gly-Thr [PSKGT]) unrelated to pentigetide A dose of 0.3 mg/kg of each peptide was used. As in the dose-response trial, solutions were administered s.c. 1 day prior to and 1 hour prior to induction of colitis and daily for a further 3 days until animals were sacrificed.

C. Results

Figure 1B:
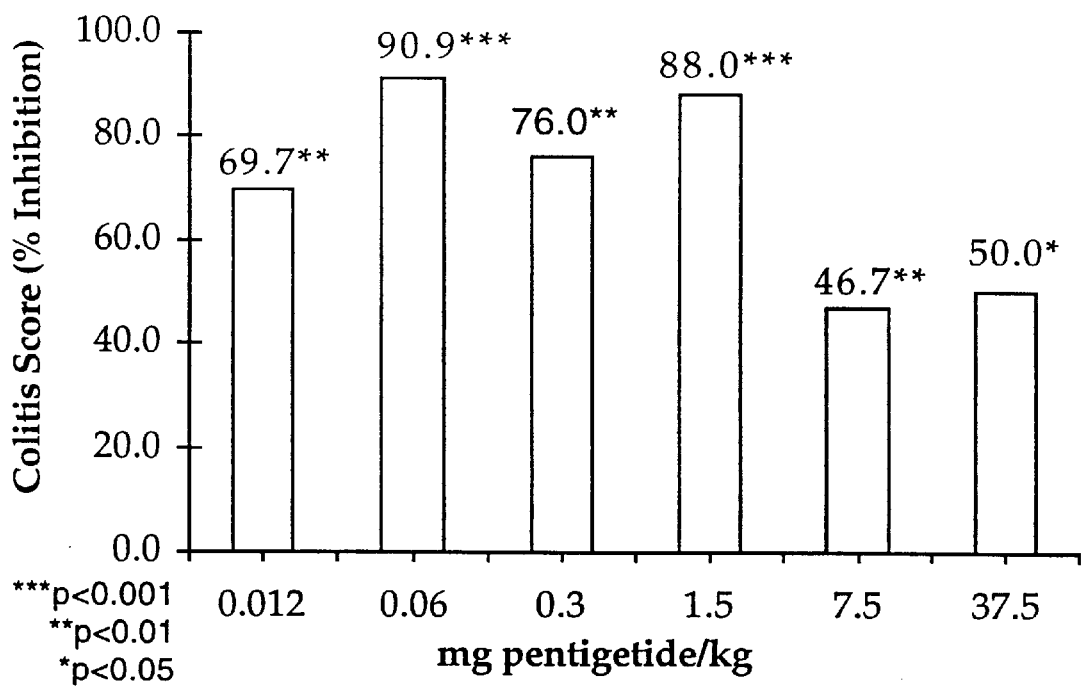

Dose Response Trial: FIGS. 1$a$ and 1$b$

FIG. 1$a$ shows percent inhibition of colonic edema in mice treated with increasing doses of pentigetide. A trend of increasing inhibition with increasing dose is evident with statistically significant inhibition (60.0%, $p<0.01$) first observed at 0.3 mg/kg. The maximum inhibitory response to pentigetide (70.0%, $p<0.01$) was observed at 1.5 mg/kg. Above this dose, the drug was decreasingly effective in reducing the edema response.

Data derived from the colitic score reveals a similar dose-response pattern (FIG. 1$b$). A significant reduction in colitic signs was produced at every dose tested. Even the lowest dose tested (0.012 mg/kg) produced a large reduction (69.7%, $p<0.01$) in the mean colitis score. Pentigetide was maximally effective at concentrations of 0.06 mg/kg (90.9%, $p<0.001$), 0.3 mg/kg (76.0%, $p<0.01$) and 1.5 mg/kg (88.0%, $p<0.001$). As noted with the edema response, above 1.5 mg/kg the drug was decreasingly effective in suppressing the signs of colitis.

Figure 2A:
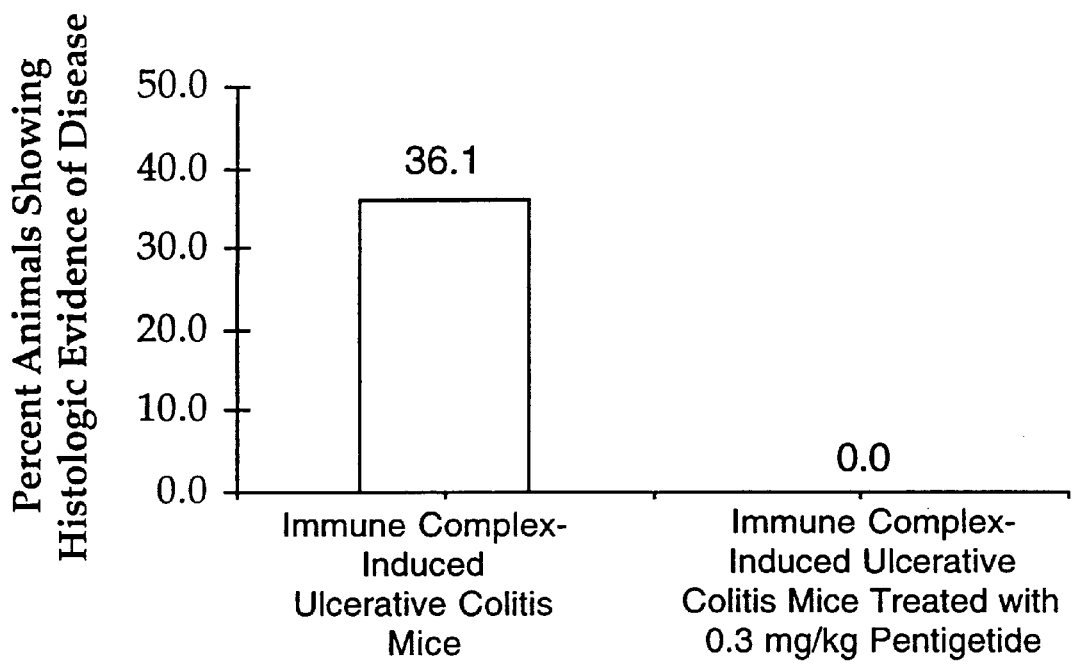
FIGS. 2a and 2b depict the inhibition by Asp-Ser-Asp-Pro-Arg of microscopic evidence of inflammation in mice in an immune complex-induced ulcerative colitis model.
Figure 2B:
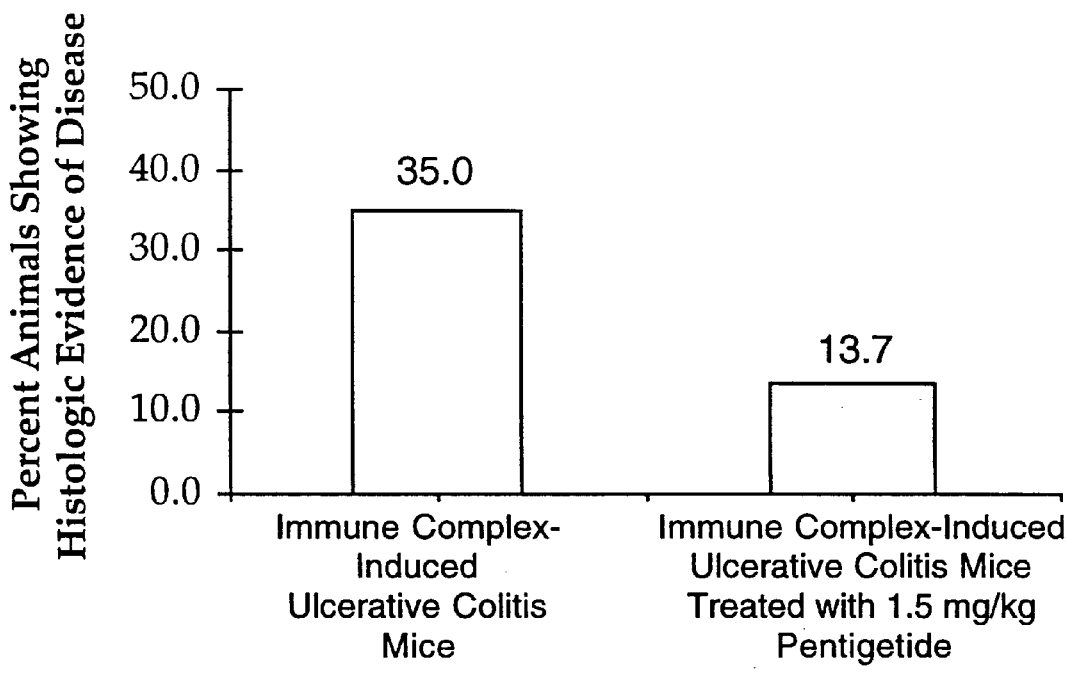

Microscopic Analysis of Therapeutic and Peptide Control Trial: FIGS. 2$a$ and 2$b$ Microscopic analysis of hematoxylin and eosin-stained slides of colonic tissues from pentigetide or saline-treated mice demonstrate that pentigetide reduced the incidence of inflammatory changes in the colon. In the studies of pentigetide-treated mice receiving 0.3 mg/kg, no inflammatory changes were observed while 36.1% of the vehicle control-treated mice exhibited microscopic signs of colon inflammation which include edema, leukocytic infiltration, mucosal atrophy, fibrosis, hemorrhage, lumenal cellular debris, necrosis and ulceration (FIG. 2$a$).

A similar reduction of microscopic lesions was observed in mice treated with 1.5 mg/kg (FIG. 2$b$). Of the vehicle control-treated mice, 35.0% had significant microscopic lesions while 13.7% of pentigetide-treated mice had lesions.

Figure 3A:
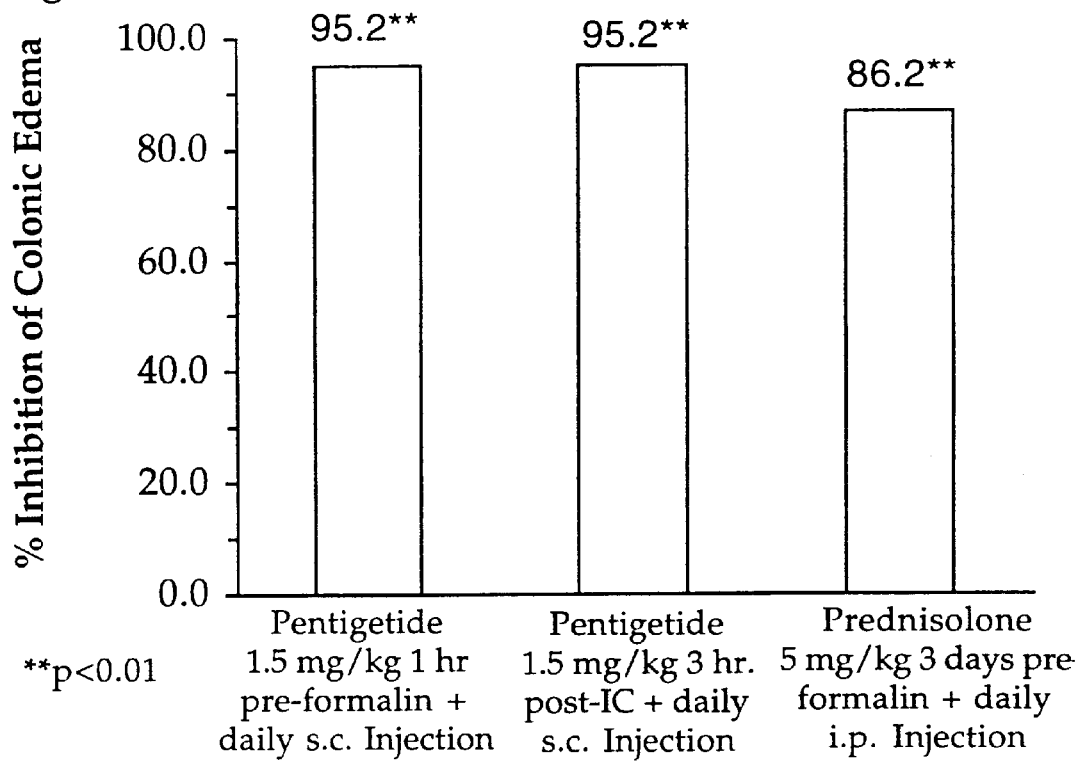
FIGS. 3a and 3b compare the inhibition by Asp-Ser-Asp-Pro-Arg and prednisolone of colonic edema and colitic signs in mice treated with Asp-Ser-Asp-Pro-Arg immediately prior to or after inflammation induction in an immune complex-induced ulcerative colitis model.
Figure 3B:
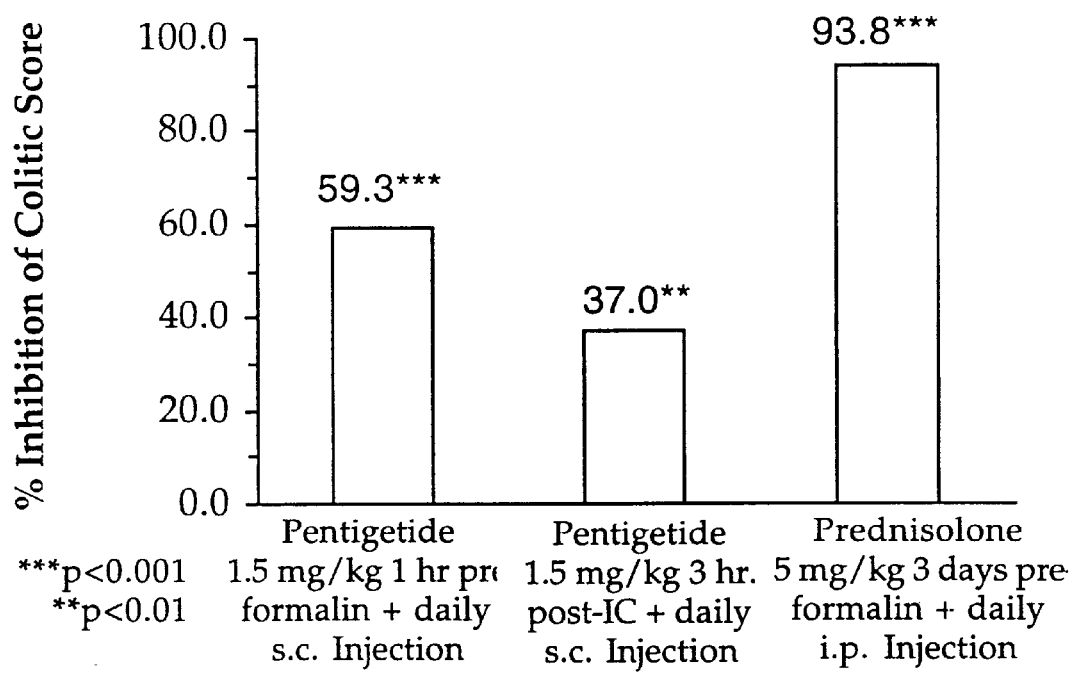

Therapeutic Trial: FIGS. 3$a$ and 3$b$

Pentigetide treatment (1.5 mg/kg) commencing either one hour prior to the initial induction of inflammation (intrarectal formalin instillation) or three hours after the administration of i.v. immune complexes (six hours after intrarectal formalin instillation) resulted in substantial and statistically significant reduction of colonic edema (FIG. 53$a$). Both dosing regimens resulted in an identical reduction of colonic edema (95.2%, $p<0.01$). Mice receiving i.p. injections of prednisolone (5.0 mg/kg) for three days prior to inflammation induction and then daily thereafter experienced a comparable reduction of colonic edema (86.2%, $p<0.01$).

The colitic sign scores of these mice were also suppressed for both dosing regimens when compared to saline-treated control mice (FIG. 3$b$). "Prophylactic" pentigetide treatment commencing one hour prior to formalin-administration resulted in a 59.3% ($p<0.001$) reduction of the colitic score while "therapeutic" pentigetide treatment resulted in a 37.0% ($p<0.01$) reduction of the colitic score. Prednisolone-treated mice experienced a 93.8% ($p<0.001$) reduction of colonic edema.

Figure 4A:
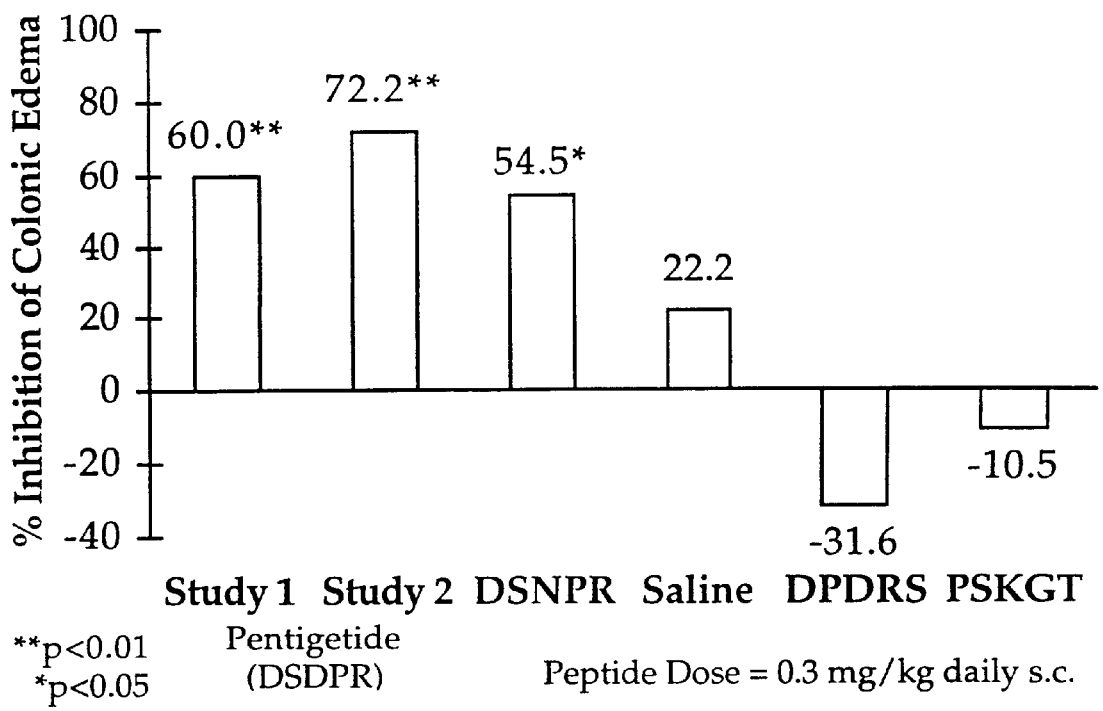
FIGS. 4a and 4b depict the inhibition by Asp-Ser-Asp-Pro-Arg (DSDPR), Asp-Ser-Asn-Pro-Arg (DSNPR) and control peptides (DPDRS and PSKGT) of colonic edema and colitis signs in mice in an immune complex-induced ulcerative colitis model.
Figure 4B:
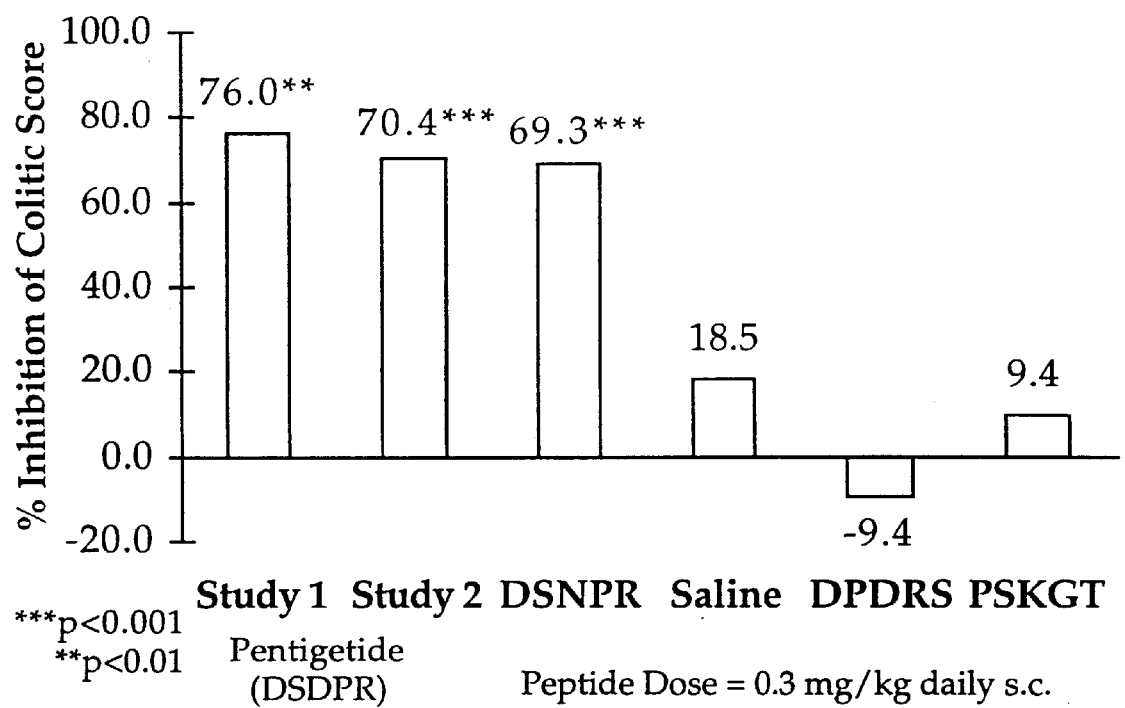

Control Peptide and Asp-Ser-Asn-Pro-Arg Trial: FIGS. 4$a$ and 4$b$

FIG. 4 illustrates the percent inhibition of colonic edema for pentigetide, Asp-Ser-Asn-Pro-Arg and two peptide controls (Asp-Pro-Asp-Arg-Ser and Pro-Ser-Lys-Gly-Thr) and saline. Only the pentigetide and Asp-Ser-Asn-Pro-Arg treated animals showed significantly reduced colonic edema with 72.2% ($p<0.01$) inhibition, and 54.5% ($p<0.05$) inhibition, respectively. This inhibition was similar to the 60.0% ($p<0.01$) inhibition observed in the first dose-response trial for the 0.3 mg/kg pentigetide dose.

Colitic sign scores, shown in FIG. 4$b$, were also significantly reduced only for those animals treated with pentigetide or Asp-Ser-Asn-Pro-Arg. Pentigetide produced 70.4% ($p<0.001$) suppression and Asp-Ser-Asn-Pro-Arg produced 69.3% ($p<0.001$) suppression. Neither of the two control peptides nor saline produced significant suppression of either edema or colitic score.

d. Conclusions

These studies demonstrate that pentigetide has a potent action in reducing objective and clinically-related signs of intestinal and rectal inflammation in a mouse model of inflammatory bowel disease (ulcerative colitis). Pentigetide may be used as a prophylactic treatment to suppress disease when administered before the initiation of intestinal inflammation. Additionally, pentigetide treatment can be used as a therapeutic treatment to suppress inflammation after it has been initiated by a disease process.

The demonstrated anti-inflammatory activity of pentigetide and the peptide Asp-Ser-Asn-Pro-Arg is related to the specific amino acid sequences of the respective peptide. Control peptides which resemble both pentigetide and Asp-Ser-Asn-Pro-Arg were inactive in these studies.

The fact that pentigetide and the peptide Asp-Ser-Asn-Pro-Arg can suppress inflammation caused by exposure to an inflammatory chemical like formalin in conjunction with immune complex-induced inflammation suggests that pentigetide and Asp-Ser-Asn-Pro-Arg may be therapeutically used to treat irritation and inflammation, particularly that of intestinal and rectal tissues, produced by either chemical exposure and/or by diseases or processes in which immune complexes and/or complement contribute to inflammation. In addition, the utility of the present compounds in treating intestinal and rectal inflammation suggests that inflammation produced by other processes, including but not limited to rectal inflammation associated with hemorrhoids and skin inflammation associated with exposure to chemical irritants such as, for example, Vitamin A and its derivatives (retinoids, including tretinoin and related compounds), may also be treated and/or prevented using pentigetide and the other compounds disclosed herein.

In the practice of the methods of the present invention, an effective amount of pentigetide, Asp-Ser-Asn-Pro-Arg, or of a particular peptide or derivative thereof, or a pharmaceutical composition containing the same, as defined above, is administered via any of the usual and acceptable methods known in the art, either singly or in combination with other compound or compounds of the present invention or other pharmaceutical agents such as antihistamines, corticosteroids, and the like. These compounds or compositions may thus be administered orally, sublingually, topically (e.g., on the skin or in the eyes), rectally (e.g., by suppository or foam), parenterally (e.g., intramuscularly, intravenously, subcutaneously or intradermally), or by inhalation, and in the form of either solid, liquid or gaseous dosage including tablets, suspensions, and aerosols as discussed in more detail hereinafter. The administration can be conducted in single unit dosage form with continuous therapy or in single dose therapy ad libitum. Administration may also be conducted in the course of a preventative treatment by application of a formulation containing both a compound of the invention and a second substance which may, itself, be a potential source of irritation, as for example a cosmetic substance or a topical skin formulation containing a Vitamin A (retinoid) substance. Examples of potentially irritating chemical components and cosmetic substances are described in applicant's U.S. Pat. No. 5,716,625 and are not repeated here.

In one preferred embodiment, the method of the present invention is practiced in a "therapeutic" manner when the relief of symptoms is specifically required or perhaps imminent; in another preferred embodiment, the method hereof is effectively practiced as continuous or prophylactic treatment.

In view of the foregoing as well as in consideration of the degree of severity of the condition being treated, age of subject, and so forth, all of which factors being determinable by routine experimentation by one skilled in the art, the effective dosage in accordance herewith can vary over a wide range. A preferred dosage in humans, depending on the disease in question, the peptide in question and the mode and schedule of administration, may vary from about 0.1 to 50 mg/kg, or more particularly 0.3 to 1.5 mg/kg, while a possible range of necessary doses may vary from about 0.1 $\mu$g/kg to 800 mg/kg.

Useful pharmaceutical carriers for the preparation of the compositions hereof, can be solids, liquids or gases; thus, the compositions can take the form of tablets, pills, capsules, powders, enterically coated or other protected formulations (such as binding on ion exchange resins or other carriers, or packaging in lipid protein vesicles or adding additional terminal amino acids or replacing a terminal amino acid in the L-form with one in the D-form), sustained release formulations solutions (e.g., ophthalmic drops), suspensions, elixirs, aerosols, and the like. The carrier can be selected from the various oils including those of petroleum, animal, vegetable or synthetic origin, for example, peanut oil, soybean oil, mineral oil, sesame oil, and the like. Water, saline, aqueous dextrose, and glycols are preferred liquid carriers, particularly (when isotonic) for injectable solutions.

Suitable pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk, glycerol, propylene glycol, water, ethanol, and the like. The compositions may be subjected to conventional pharmaceutical expedients such as sterilization and may contain conventional pharmaceutical additives such as preservatives, stabilizing agents, wetting or emulsifying agents, salts for adjusting osmotic pressure, buffers, and the like. Suitable pharmaceutical carriers and their formulations are described in "Remington's Pharmaceutical Sciences" by E. W. Martin. Such compositions will, in any event, contain an effective amount of the active compound together with a suitable amount of carrier so as to prepare the proper dosage form for proper administration to the host.

To be effective for the prevention or treatment of inflammatory diseases it is important that the therapeutic agents be relatively non-toxic, non-antigenic and non-irritating at the levels in actual use.

The present peptides may be synthesized by the solid phase peptide synthesis method, as described for example in Merrifield, J. Am. Chem. Soc., 85, 2149–2154 (1963); Meienhofer in "Hormonal Proteins and Peptides," ed. C.H. Li, Vol. 2 (Academic Press, 1973), pp. 48–267; and Barany and Merrifield in "The Peptides," eds. E. Gross and J. Meienhofer, Vol. 2 (Academic Press, 1980), pp. 3–285.

Exemplary solid phase methods for synthesizing the present peptides are given in U.S. Pat. No. 4,816,449 and are not repeated here. Methods for preparation of substituted peptides as disclosed herein are also given in that patent.

It is understood that various other modifications will be apparent to and can readily be made by those skilled in the art without departing from the scope and spirit of this invention. Accordingly, it is not intended that the scope of the claims appended hereto be limited to the description as set forth above, but rather that the claims be construed as encompassing all the features of patentable novelty which reside in the present invention, including all features which would be treated as equivalents thereof by those skilled in the art to which this invention pertains.

What is claimed is:

1. A composition for the treatment of a chemically-induced, non-IgE-mediated irritation or inflammation condition comprising a chemical component which is a potential source of irritation or inflammation, and a therapeutically effective amount of a peptide, or a pharmaceutically acceptable salt thereof, said peptide having the amino acid sequence Asp-Ser-Asp-Pro-Arg or Asp-Ser-Asn-Pro-Arg, and a pharmaceutically acceptable carrier.

2. A composition for the treatment of a chemically-induced, non-IgE-mediated irritation or inflammation condition comprising a therapeutically effective amount of a derivatized peptide, or a pharmaceutically acceptable salt thereof, said derivatized peptide comprising the amino acid sequence Asp-Ser-Asp-Pro-Arg or Asp-Ser-Asn-Pro-Arg, formed with a pharmaceutically acceptable substituent selected from $N^{\alpha}$-substituents of the form RCO— and R—, and C-terminal substituents of the form —NH$_2$,— NHNH$_2$,—NHR, —NR$_2$ and —OR (where each R is independently selected from unbranched and branched, unsubstituted and substituted lower alkyl, alkenyl and alkynyl groups of from 1 to about 8 carbons, aryl, alkaryl, aralkyl and cycloalkyl groups of from about 6 to about 18 carbons, and in the case of—NR$_2$, from cyclized groups forming (in attachment with the nitrogen atom) a 5–8 membered saturated heterocyclic ring optionally containing an oxygen or nitrogen as a further ring heteroatom), or formed with des-alpha-amino derivatives of one or more amino acid residues in said peptide, and a pharmaceutically acceptable carrier.

3. The composition of claim 2 wherein said composition is for the prevention of said chemically-induced, non-IgE-mediated irritation or inflammation.

4. The composition of claim 1 wherein said composition is a topical composition.

5. The composition of claim 2 wherein said composition is a topical composition.

6. The composition of claim 2 further comprising a chemical component which is a potential source of irritation or inflammation.

7. The composition of claim 1 further comprising a cosmetic substance.

8. The composition of claim 2 further comprising a cosmetic substance.

9. A method for the treatment of chemically-induced, non-IgE-mediated irritation or inflammation comprising administering to a mammalian subject a chemical component which is a potential source of irritation or inflammation and, in a pharmaceutically acceptable carrier, a therapeutically effective amount of a peptide, or a pharmaceutically acceptable salt thereof, said peptide having the amino acid sequence Asp-Ser-Asp-Pro-Arg or Asp-Ser-Asn-Pro-Arg.

10. A method for the treatment of chemically-induced, non-IgE-mediated irritation or inflammation comprising administering to a mammalian subject, in a pharmaceutically acceptable carrier, a therapeutically effective amount of a derivatized peptide, or a pharmaceutically acceptable salt thereof, said derivatized peptide comprising the amino acid sequence Asp-Ser-Asp-Pro-Arg or Asp-Ser-Asn-Pro-Arg, formed with a pharmaceutically acceptable substituent selected from $N^{\alpha}$-substituents of the form RCO— and R—, and C-terminal substituents of the form —$NH_2$, —$NHNH_2$, —NHR, —$NR_2$ and —OR (where each R is independently selected from unbranched and branched, unsubstituted and substituted lower alkyl, alkenyl and alkynyl groups of from 1 to about 8 carbons, aryl, alkaryl, aralkyl and cycloalkyl groups of from about 6 to about 18 carbons, and in the case of —$NR_2$, from cyclized groups forming (in attachment with the nitrogen atom) a 5–8 membered saturated heterocyclic ring optionally containing an oxygen or nitrogen as a further ring heteroatom), or formed with des-alpha-amino derivatives of one or more amino acid residues in said peptide.

11. The method of claim 10 wherein said administration is for the prevention of said chemically-induced, non-IgE-mediated irritation or inflammation.

12. The method of claim 9 wherein said administration is topical.

13. The method of claim 10 wherein said administration is topical.

14. The method of claim 10 further including administering a chemical component which is a potential source of irritation or inflammation.

15. The method of claim 9 further including administering a cosmetic substance.

16. The method of claim 10 further including administering a cosmetic substance.

* * * * *